US011004544B2

(12) United States Patent
Yang et al.

(10) Patent No.: US 11,004,544 B2
(45) Date of Patent: May 11, 2021

(54) METHOD OF PROVIDING BIOLOGICAL DATA, METHOD OF ENCRYPTING BIOLOGICAL DATA, AND METHOD OF PROCESSING BIOLOGICAL DATA

(71) Applicants: MACROGEN, INC., Seoul (KR); PSOMAGEN, INC., Rockville, MD (US)

(72) Inventors: Joshua Sungwoo Yang, Bucheon-si (KR); Jaekyung Chon, Seoul (KR); Ik Jung Choi, Seoul (KR); Hyun Min Park, Seoul (KR); Jieun Park, Seoul (KR); Jeongsun Seo, Seoul (KR); Changhoon Kim, Gwangmyeong-si (KR); Han Sol Seo, Yongin-si (KR); Jiwon Shin, Gunpo-si (KR); In Hee Hwang, Seoul (KR); Seon Hye Sim, Seoul (KR); Chang Woo Cho, Anyang-si (KR); Nam Hee Kim, Seoul (KR); Hye Eun Lee, Seoul (KR); Kyuin Hwang, Incheon (KR)

(73) Assignees: MACROGEN, INC., Seoul (KR); PSOMAGEN, INC., Rockville, MD (US)

( * ) Notice: Subject to any disclaimer, the term of this patent is extended or adjusted under 35 U.S.C. 154(b) by 0 days.

(21) Appl. No.: 16/743,514

(22) Filed: Jan. 15, 2020

(65) Prior Publication Data
US 2020/0303040 A1 Sep. 24, 2020

(30) Foreign Application Priority Data
Mar. 21, 2019 (KR) .......................... 10-2019-0032136

(51) Int. Cl.
*H04L 9/08* (2006.01)
*G16B 50/40* (2019.01)
(Continued)

(52) U.S. Cl.
CPC ............. *G16B 50/40* (2019.02); *G16B 40/00* (2019.02); *H04L 9/0866* (2013.01); *H04L 9/3242* (2013.01)

(58) Field of Classification Search
CPC ....... G16B 50/40; G16B 40/00; H04L 9/0866; H04L 9/3242
See application file for complete search history.

(56) References Cited

U.S. PATENT DOCUMENTS 9,942,206 B1 * 4/2018 Miller .................. H04L 9/3239
2015/0236849 A1 * 8/2015 Ayday .................. H04L 9/0819
713/193
(Continued)

FOREIGN PATENT DOCUMENTS

CN 105719131 A 6/2016
JP 2008-090716 A 4/2008
(Continued)

OTHER PUBLICATIONS

Extended European Search Report for related EP application No. 20151174.8 dated May 29, 2020 from European Patent Office.
(Continued)

*Primary Examiner* — Olugbenga O Idowu
(74) *Attorney, Agent, or Firm* — Paratus Law Group, PLLC

(57) ABSTRACT

Disclosed is a method of providing biological data. The method includes the following steps performed by a data processing device: selecting a biological data set from a biological data pool; encrypting biological data included in the biological data set to produce encrypted biological data; transferring the encrypted biological data to a user; receiving a result of analysis on the encrypted biological data from the user; and transferring information on the encrypted biological data included in the result of the analysis to the user. The data processing device encrypts the biological data with a
(Continued)

key determined according to a combination of biological data constituting the biological data set.

14 Claims, 8 Drawing Sheets

(51) Int. Cl.
*G16B 40/00* (2019.01)
*H04L 9/32* (2006.01)

(56) References Cited

U.S. PATENT DOCUMENTS

| | | | |
|---|---|---|---|
| 2017/0242961 A1 | 8/2017 | Shukla et al. | |
| 2020/0076798 A1* | 3/2020 | Lidsky | H04L 9/3231 |

FOREIGN PATENT DOCUMENTS

| | | |
|---|---|---|
| JP | 2014-096692 A | 5/2014 |
| JP | 2017-223784 A | 12/2017 |
| KR | 10-0537523 B1 | 12/2005 |
| KR | 10-2009-0068686 A | 6/2009 |
| KR | 10-1880175 B1 | 7/2018 |

OTHER PUBLICATIONS

D Rachmawati et al., "A comparative study of Message Digest 5(MD5) and SHA256 algorithm", Journal of Physics: Conference Series, Mar. 1, 2018, pp. 1-7, vol. 978.
Korean Office Action for related KR Application No. 10-2019-0032136 dated May 15, 2019 from Korean Intellectual Property Office.
Korean Notice of Allowance for related KR Application No. 10-2019-0032136 dated Sep. 20, 2019 from Korean Intellectual Property Office.
Erman Ayday et al, "Cryptographic Solutions for Credibility and Liability Issues of Genomic Data", IEEE Transactions on Dependable and Secure Computing, Jan. 2019, pp. 33-43, vol. 16, No. 1.
Japanese Office Action for related JP application No. 2019-234665 dated Nov. 4, 2020 from Japanese Patent Office.

* cited by examiner

FIG. 5A

| original genotype data | | | encrypted genotype data | |
|---|---|---|---|---|
| genetic identifier | genetic location information | variant information | genetic identifier and genetic location | variant information |
| 1 | 323342 | AA | 111010101011101 | 11 |
| 2 | 1234513 | AT | 101110100011111 | 01 |
| X | 23534 | GC | 010010101010100 | 10 |
| MT | 12030 | CC | 111011101001100 | 00 |

FIG. 5B

| original phenotype data | | encrypted phenotype data |
|---|---|---|
| item | information | |
| sex | male, female | 0,1 |
| race | Asian, Korean, ... | 001,011,000 |
| height | 183, 160,... | 101001, 100110,.. |
| medication | antibiotics and Aspirin,... | 1000110, 1110110, .. | ic
METHOD OF PROVIDING BIOLOGICAL DATA, METHOD OF ENCRYPTING BIOLOGICAL DATA, AND METHOD OF PROCESSING BIOLOGICAL DATA

ACKNOWLEDGEMENT

This work was supported by an Institute for Information & Communications Technology Promotion (IITP) grant funded by the Korean government, Ministry of Science and ICT (MSIT), under an Information Technology Research Center (ITRC) support program (No. IITP-2018-0-0144). This work was also supported by a Korea Technology & Information Promotion Agency for SMEs (TIPA) grant funded by the Korean government, Small and Medium Business Administration (SMBA), under a World Class 300 Project R&D support program (1425121126 [S2638360], Development of precise diagnosis system and technology of gastrointestinal cancer by constructing personal genome big data).

CROSS REFERENCE TO RELATED APPLICATION

This application claims priority to and the benefit under 35 U.S.C. § 119(a) of Korean Patent Application No. 10-2019-0032136, filed Mar. 21, 2019, in the Korean Intellectual Property Office, the entire disclosure of which is incorporated herein by reference for all purposes.

BACKGROUND

The following description relates to a technique of providing biological data. More particularly, the following description relates to a technique of dynamically encrypting biological data and providing the encrypted biological data.

Techniques for studying genetic variations of individuals have evolved rapidly since the early 2000s when human genome sequences were identified. For example, due to development of technologies for massive detection of single nucleotide polymorphisms (SNPs), hundreds of thousands of genetic variations can be rapidly determined at low cost. Genome-wide association study (GWAS) refers to the research field in which hundreds of thousands of SNPs are obtained through next generation sequencing (NGS) and genetic variations that are statistically significantly associated with phenotypes are found among the SNPs.

Information on phenotypes and their associated genetic variations of individuals is personal information. Thus, an access to phenotype data and genotype data of individuals is an important issue in a variety of genetic analysis methods. A massive amount of phenotype and genotype data has been recently published and shared by a number of researchers. Therefore, there is a high risk that third parties may have access to the data.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The following description provides a technique of providing personal genotype and phenotype data to a specific researcher while preventing a third party from having access to the data. The present disclosure described hereinafter provides a technique of performing genomic analysis on encrypted data.

In one general aspect, there is provided a method of providing biological data, the method including: acquiring, by a data processing device, a biological dataset selected from a biological dataset pool; encrypting, by the data processing device, biological data included in the biological dataset; transferring, by the data processing device, the encrypted biological data to a user; receiving, by the data processing device, a result of analysis on the encrypted biological data from the user; and transferring, by the data processing device, information on encrypted biological data included in the result of analysis to the user. The data processing device may encrypt the biological data by using a key determined depending on a combination of biological data constituting a biological dataset.

In another aspect, there is provided a method of encrypting biological data, the method including: receiving, by a data processing device, a biological data pool; selecting, by the data processing device, a biological dataset from the biological data pool according to classification information; and encrypting, by the data processing device, biological data included in the biological dataset. The encrypting is performed with a key that is determined depending on a combination of biological data constituting the biological dataset.

In yet another aspect, there is provided a biological data processing device including: a program configured to encrypt biological data included in a biological dataset; a storage device for storing a biological data pool; and an computation device for selecting a biological dataset from the biological data pool according to classification information and encrypting biological data included in the biological dataset selected by the program. The encrypting is performed with a key that is determined depending on a combination of biological data constituting a biological dataset.

BRIEF DESCRIPTION OF THE DRAWINGS

FIGS. 5A and 5B are diagrams illustrating examples of original biological data and encrypted biological data;

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
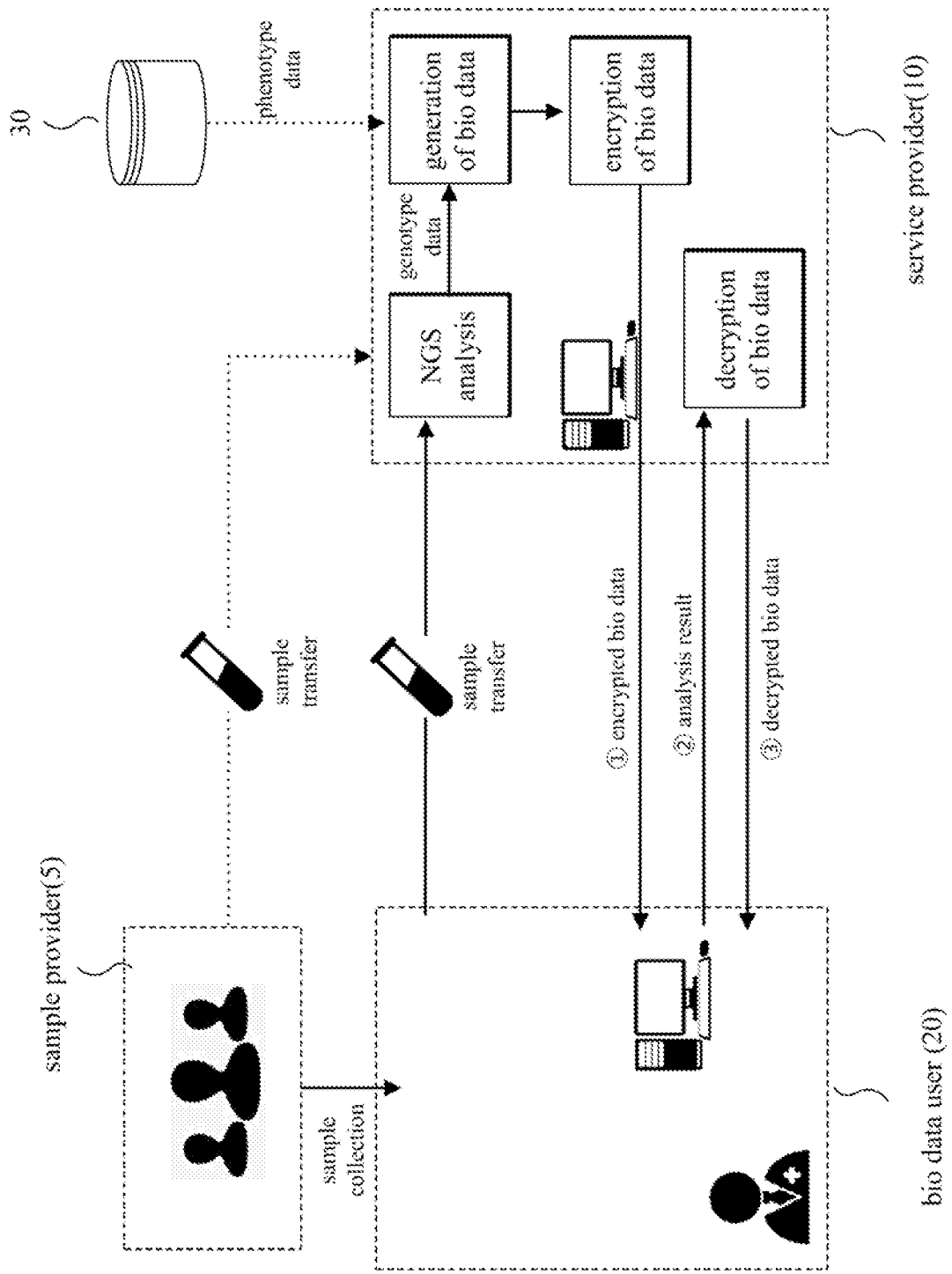
FIG. 1 is a diagram illustrating a biological data processing method according to one embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

As used herein, the term "and/or" includes any one and any combination of any two or more of the associated listed items.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Terms and words used herein will be described first.

A sample may refer to a single cell or multiple cells, a cell fragment, or a body fluid taken from a subject to be analyzed.

A subject may refer to a cell, tissue, organ, or organism. A subject may be a human subject but is not limited thereto. Subjects may include animals, plants, microorganisms, and the like.

Genotype data or genomic information may refer to information on a genome obtained from a sample of a particular subject. For example, genotype data includes deoxy ribonucleic acid (DNA), ribonucleic acid (RNA), protein sequences, gene expression data, genetic mutation from reference genome data, DNA methylation, and the like. In general, genotype data includes sequence information obtained by analyzing a particular sample. Genotype data is typically expressed as digital data. Sequence data obtained by using an NGS analyzer corresponds to genotype data.

Phenotype data or phenotypic information may refer to expressed traits (phenotypes) of a living body. Phenotype data means external expressions of a cell, tissue, or subject. For example, in the case of a human individual, phenotype data may include measurements such as height and weight and survey data such as sex, race, disease status, and health condition (disease).

The phenotype data may include other types of data used to determine the health condition of individuals. For example, the phenotype data may include medical data such as electronic medical records (EMR). Medical data may include health check results (clinical information) generated by medical equipment or diagnosis results generated by medical staff. For example, the medical data may include image data acquired from medical equipment. In addition, the medical data may include bio-signal data measured with health medical equipment. In addition, the medical data may include lifestyle data (activity pattern, momentum, etc.) measured with IoT devices.

Biological data (also called bio data) may be a term covering genotype data, phenotype data, biological data, and medical data. The biological data may include at least one type of data selected from among genotype data, phenotype data, biometric data, and medical data.

A sample provider is a subject that provides a sample for analysis of genotype data. For example, the sample provider may be an individual or a medical facility. Alternatively, the sample provider may be a research institution or an analysis company for analyzing samples.

A biological data provider is an entity that analyzes a sample and produces biological data such as genotype data. For example, the biological data provider produces genotype data which is also called genetic data or genomic data through next generation sequencing (NGS). The biological data provider produces biological data by combining genotype data and phenotype data.

A biological data user is an entity that uses biological data. The biological data user may be an entity that performs an analysis on biological data. For example, the biological data user may be a medical facility, an analysis company, or the like. The biological data user may perform GWAS-based analysis.

A service provider is an entity that processes biological data in a predetermined manner. The service provider is not an entity that analyzes biological data but is an entity that process biological data in a predetermined manner and provides the processed biological data to the biological data user. Biological data processing includes encryption, pre-processing, and post-processing of biological data. For example, the service provider may encrypt biological data in whole or in part and provide the entirely or partially encrypted biological data to the biological data user. In addition, the service provider may convert the encrypted biological data into a predetermined form of biological data and provide the predetermined form of biological data resulting from the conversion. The service provider is an entity that treats, processes, and encrypts biological data in a predetermined manner.

In some cases, the service provider produces biological data. In these cases, the service provider provides a service of processing biological data that is generated by itself. Hereinafter, a biological data service provided by the service provider will be described.

FIG. 1 is a diagram illustrating a biological data processing method according to one embodiment. The biological data processing method performed over time will be described. FIG. 1 illustrates a sample provider 5, a service provider 10, and a biological data user 20. The service provider 10 provides a service of generating biological data from a sample and providing the generated biological data.

The service provider 10 receives a sample from the sample provider 5. Alternatively, the service provider 10 may receive a sample from the biological data user 20. That is, the biological data user 20 may collect samples and provide the collected samples to the service provider 10.

The service provider 10 generates biological data first. The service provider 10 generates genotype data through next-generation sequencing (NGS). There are other various ways to generate genotype data from a sample. The service provider 10 acquires phenotype data of the sample provider 5. For example, the service provider 10 acquires the phenotype data of a specific sample provider from a medical database 30 such as EMR. In this case, the service provider 10 acquires specific phenotype data matched with an identifier of a sample or a sample provider from the medical database 30. The phenotype data includes at least one type of information selected from among physical information, bio-signal information, medical information, and diagnosis information. The service provider 10 generates biological data on the basis of at least one type of data selected from among genotype data and phenotype data. Alternatively, the service provider 10 may generate biological data consisting of only genotype data. The biological data may be digital data.

The service provider 10 processes the biological data in a predetermined manner. Typically, the service provider 10 encrypts the biological data. The service provider 10 fully or partially encrypts the biological data to produce encrypted biological data. The details of the encryption process will be described later.

The service provider 10 transfers the encrypted biological data to the biological data user 20. The biological data user 20 may analyze the biological data that is in an encrypted form. The biological data has a predetermined digital data format. The genotype data is specified by the location of a gene or a sequence fragment or by the type or base sequence of a gene. The service provider 10 encrypts the same original value (for example, "AGC") into the same encrypted data (for example, "011110"). The biological data user 20 extracts a predetermined pattern or information occurring at a specific position from the encrypted data. The biological data user 20 may derive analysis results directly from the encrypted data in the manner described above. For example, the biological data user 20 derives a repeated specific sequence, a sequence present at a specific position, a statistically significant SNP pattern, and the like as the analysis results.

The biological data user 20 transfers the analysis results to the service provider 10. The service provider 10 decrypts the encrypted biological data included in the analysis results through a predetermined decryption method. The decryption process will be described later. The service provider 10 forwards all of the analysis results or the original biological data obtained by decrypting specific biological data included in the analysis results to the biological data user 20. For example, the service provider 10 transfers a specific SNP pattern to the biological data user 20. The biological data user 20 receives the decrypted biological data and derives a final analysis result. For example, the biological data user 20 diagnoses a specific disease for a specific sample (individual) on the basis of the sequences or SNP patterns received. Alternatively, the biological data user 20 may perform genome-wide association study (GWAS) over a biological data pool.

Figure 2:
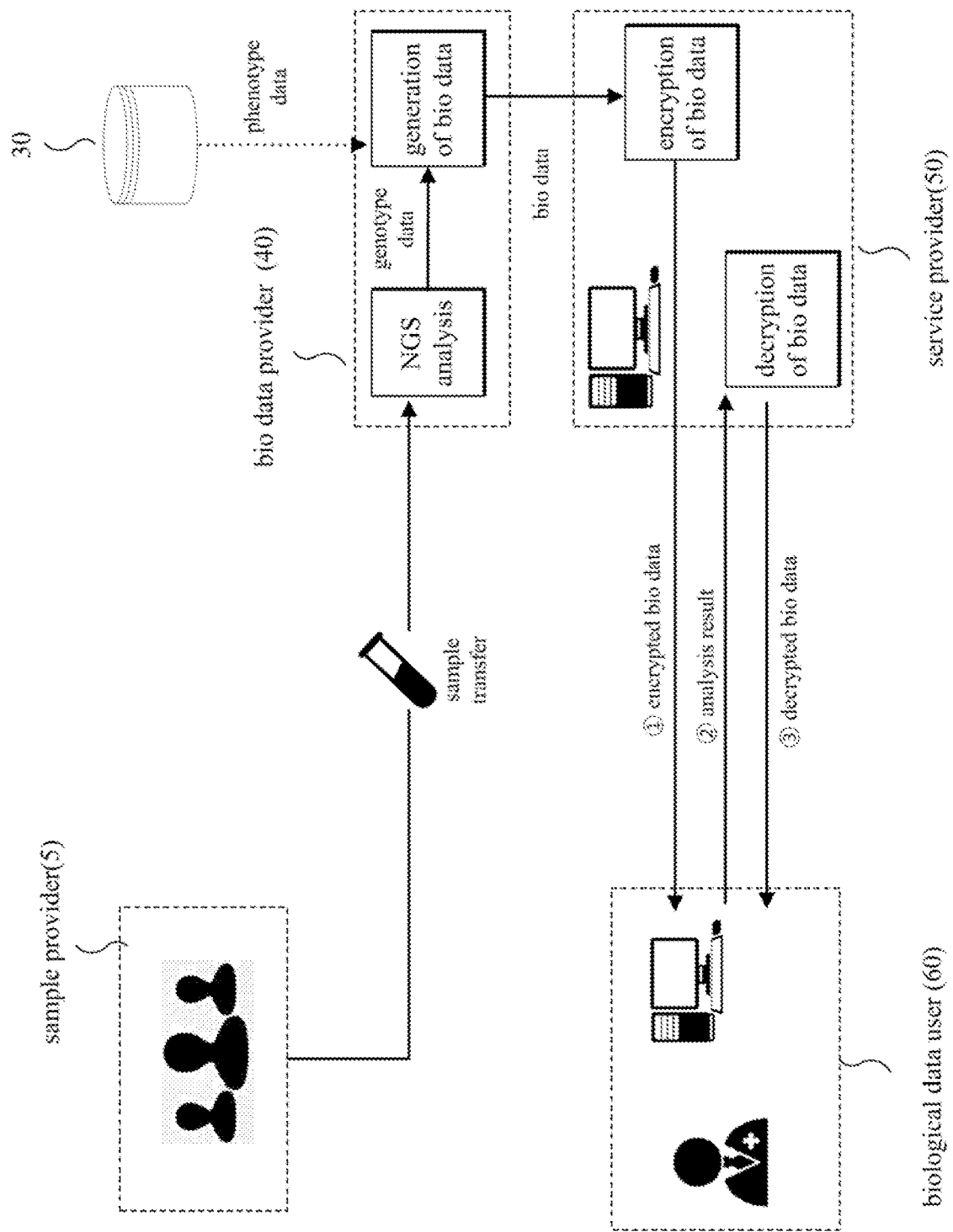
FIG. 2 is a diagram illustrating a biological data processing method according to another embodiment.

FIG. 2 is a diagram illustrating a biological data processing method according to another embodiment. FIG. 2 illustrates a sample provider 5, a biological data provider 40, a service provider 50, and a biological data user 60. FIG. 2 illustrates a case in which the biological data provider 40 and the service provider 50 are different entities. The method will be described according to the passage of time.

The biological data provider 40 receives a sample from the sample provider 5. Alternatively, the biological data provider 40 may receive a sample from the biological data user 60 as in the case of FIG. 1.

The biological data provider 40 generates biological data. That is, the biological data provider 40 generates genotype data through NGS analysis. There are other various ways to generate the genotype data besides the NGS analysis. The biological data provider 40 acquires phenotype data of the sample provider 5. For example, the biological data provider 40 acquires the phenotype data of a specific sample provider from a medical database 30, such as EMR. In this case, the biological data provider 40 acquires specific phenotype data matched with an identifier of a specific sample or a specific sample provider from the medial database 30. The phenotype data includes at least one type of information selected from among physical information, bio-signal information, medical information, and diagnosis information. The biological data provider 40 generates biological data on the basis of at least one type of data selected from among genotype data and phenotypic data.

The biological data provider 40 may generate biological data composed of only genotype data. The biological data may be digital data.

The service provider 50 processes the biological data in a predetermined manner. For example, the service provider 50 encrypts the biological data to produce encrypted biological data. The service provider 50 fully or partially encrypts the biological data to produce encrypted biological data. The encryption process will be described later.

The service provider 50 transfers the encrypted biological data to the biological data user 60. The biological data user 60 analyzes the encrypted biological data as it is. That is, the biological data user 60 analyzes the biological data that is in an encrypted form. The biological data user 60 may derive analysis results on the basis of the encrypted data. For example, the biological data user 60 derives specific sequences that are repeated, sequences present at specific positions, and statistically significant SNPs as the analysis results.

The biological data user 60 forwards the analysis results to the service provider 50. The service provider 50 decrypts the encrypted biological data present in the analysis results. The decryption process will be described later. The service provider 50 forwards the analysis results as they are to the biological data user 60 or forwards original biological data obtained by decrypting the specific biological data contained in the analysis results to the biological data user 60. For example, the service provider 50 forwards a specific SNP pattern to the biological data user 60. The biological data user 60 receives the decrypted biological data and derives a final analysis result. For example, the biological data user 60 diagnoses a specific disease for a specific sample (individual) on the basis of the SNP sequences or patterns received. Alternatively, the biological data user 20 performs genome-wise association study (GWAS) over a biological data pool.

Figure 3:
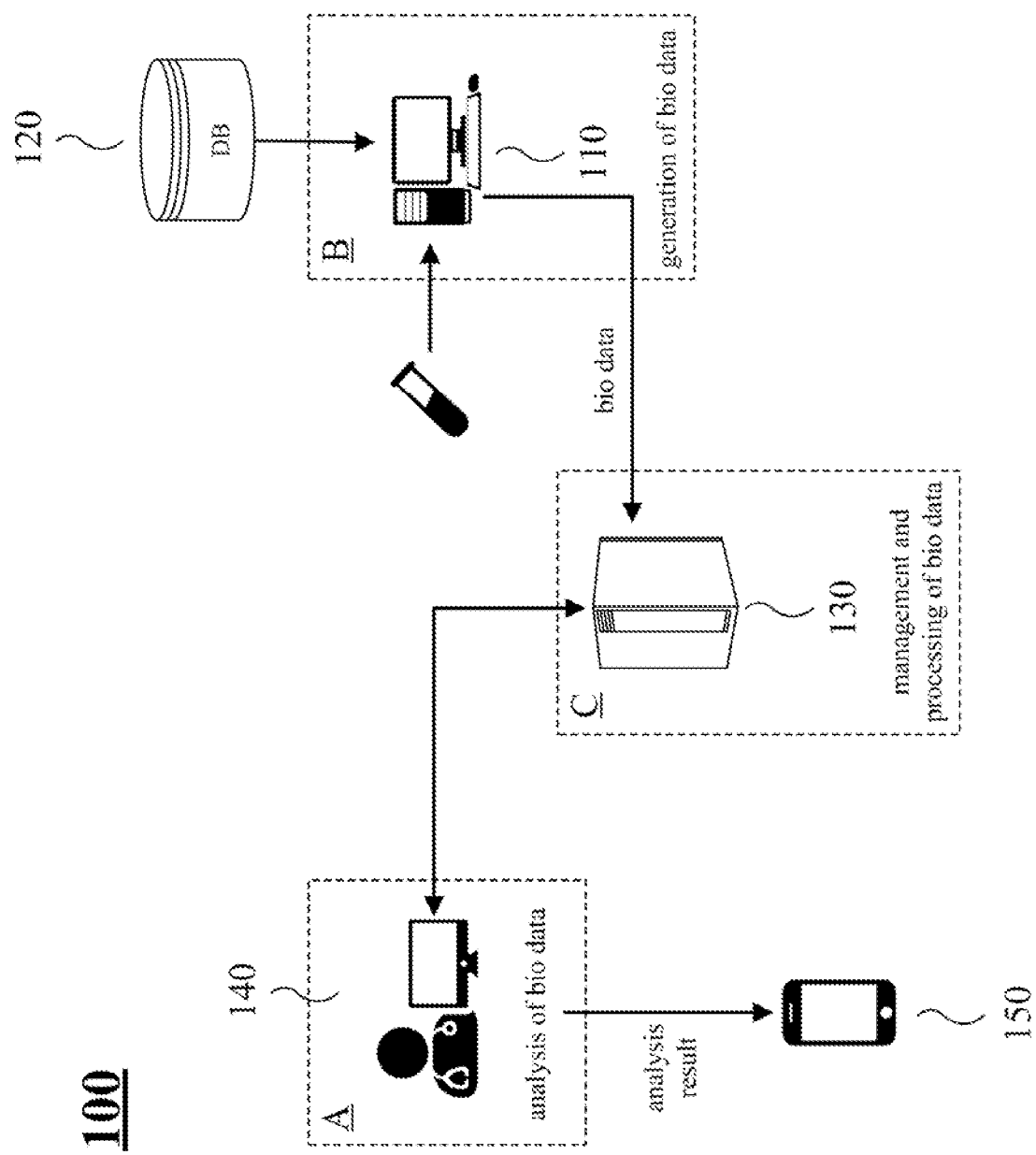
FIG. 3 is a diagram illustrating a biological data processing system according to one embodiment.

FIG. 3 is a diagram illustrating a biological data processing system 100 according to one embodiment. FIG. 3 illustrates a biological data user A, a biological data provider B, and a service provider C. The biological data user A, the biological data provider B, and the service provider C respectively correspond to an analysis device, a user terminal device, and a server in the system 100.

The biological data processing system 100 includes a data generation device 110, a data processing device 130, and a data analysis device 140. The data generation device 110 may be an analyzer for analyzing a sample. For example, the data generation device 100 includes an NGS analyzer. The data generation device 100 generates genotype data. In addition, the data generation device 110 receives phenotype data of a specific person who is a subject to be analyzed from a medical database 120. The data generation device 110 generates biological data composed of genotype data and phenotypic data. Alternatively, the data generation device 110 may generate biological data composed of only genotype data.

The data processing device 130 processes the biological data generated by the data generation device 110. The data processing device 130 encrypts the biological data, in whole or in part. The data processing device 130 may hash the biological data with the use of a predetermined hash key.

The data analysis device 140 can perform data analysis on the encrypted biological data. The data analysis device 140 transmits an analysis result to the data processing device 130. The data processing device 130 decrypts the encrypted biological data included in the analysis result in a predetermined manner. Then, the data processing device 130 transmits the decrypted biological data to the data analysis device 140. The data analysis device 140 transmits a final analysis result to a user terminal 150. The user terminal 150 refers to a person or entity having requested the analysis.

Figure 4:
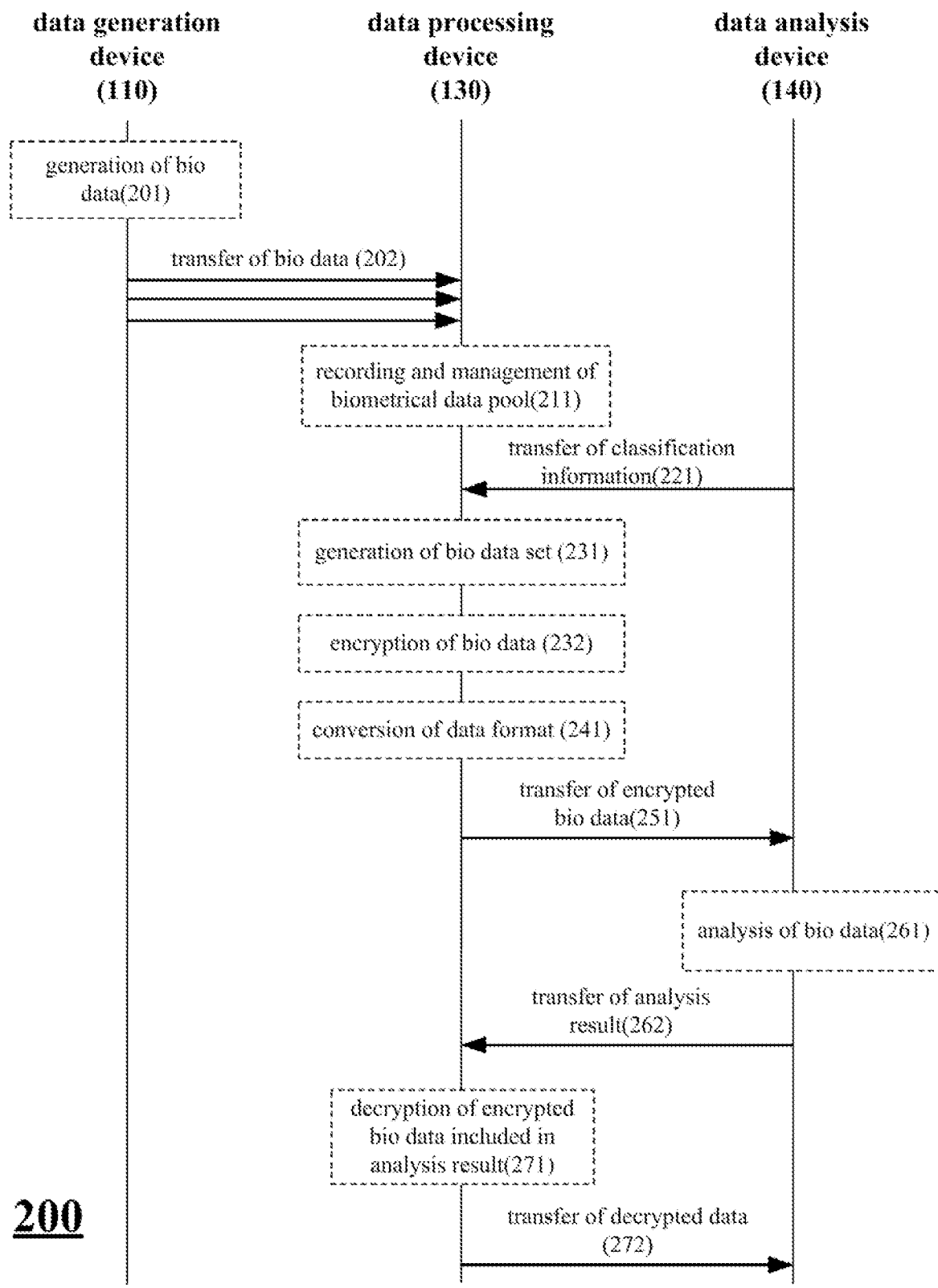
FIG. 4 is a diagram illustrating an operation flow of a biological data processing system according to one embodiment.

FIG. 4 is a diagram illustrating an operation flow 200 of the biological data processing system 100. The data generation device 110 generates biological data (Operation 201). The data generation device 110 transmits biological data to the data processing device 130. The data generation device 110 transfers biological data of a number of samples to the data processing device 130. The data processing device 130 stores and manages a biological data pool (Operation 211). The data processing device 130 may store the biological data in a storage medium isolated from an external network. The data processing device 130 may separately store genotype data and phenotypic data.

The data generation device 110 encrypts the biological data in a predetermined manner to produce encrypted biological data and transmits the encrypted biological data to data processing device 130. The data processing device 130 decrypts the encrypted biological data and stores the unencrypted biological data. In this case, a public key-based encryption and decryption scheme may be used. A public key is a key used to encrypt data, and an encryption key is a key used to decrypt encrypted data. A public key and an encryption key are provided as a key pair and are arbitrarily generated through one of various public key encryption methods (for example, RSA, elliptic curve cryptography, etc.).

The data processing device 130 receives classification information from the data analysis device 140 (Operation 221). Alternatively, the data processing device 130 may acquire the classification information from the data generation device 110.

The data processing device 130 generates a biological data set by selecting biological data from the biological data pool according to the classification information (Operation 231). The biological data set is composed of a plurality of biological data entries. The biological data set is composed of biological data entries, each entry corresponding to a different subject (i.e., an individual). The data processing device 130 selects biological data entries from the biological data pool according to certain criteria which means the classification information.

The data processing device 130 encrypts the biological data entries included in the biological data set (Operation 232). The data processing device 130 encrypts biological data, in whole or in part. The data processing device 130 uses a hash key to encrypt the biological data. The data processing device 130 determines the hash key according to a combination of biological data entries constituting the biological data set. Alternatively, the data processing device 130 may determine the hash key according to the classification information. That is, the hash key is not a fixed value but a variable value that is determined depending on the configuration of the biological data set.

The data processing device 130 transfers the encrypted biological data to the data analysis device 140. At this time, if necessary (optionally), the data processing device 130 converts the encrypted biological data into a data format required by the data analysis device 140 (Operation 241).

The data analysis device 140 analyzes the biological data by using the encrypted biological data (Operation 261). The data analysis device 140 analyzes the encrypted biological data as it is. The data analysis device 140 transmits the results of analysis to the data processing device 130 (Operation 262).

The data processing device 130 decrypts the encrypted biological data contained in the analysis results (Operation 271). The data processing device 130 has a mapping table in which original values of the biological data are associated with hashed values of the biological data. The biological data can be mapped to produce a mapping table having a predetermined size because it has values in a predetermined range. The data processing device 130 can convert the hashed biological data back into the original biological data on the basis of the mapping table. The data processing device 130 transfers the decrypted data to the data analysis device 140 (Operation 272).

The data processing device 130 provides the encrypted biological data to the data analysis device 140. The data analysis device 140 analyzes the encrypted biological data. Although the encrypted biological data is leaked to an unauthorized third party, the third party cannot identify a person corresponding to the disclosed biological data.

Examples of the encrypted data will be described below.

FIGS. 5A and 5B are diagrams illustrating an example of original biological data and encrypted biological data.

FIG. 5A illustrates an example of encrypted genotype data. Original genotype data may include a genetic identifier (ID), genetic location information, and genetic variant information. The genetic ID represents the type and location of a gene in a cell. For example, in the case of a human sample, the genetic ID includes a value in a range of 1 to 22 representing a modal number of homologous chromosomes, X representing X chromosome, Y representing Y chromosome, or MT representing mitochondria. The genetic location information indicates a position on the entire genome of a sample (subject). For example, in the case of a human sample, the genetic location information may be a value within a range of 1 to 3,000,000,000. The genetic variant information represents genome sequence information. In the case of SNPs, the genetic variant information refers to one or more bases that differ between nucleotide sequences.

The genetic variant information includes information on difference between a reference sequence and a target sequence to be analyzed.

The data processing device may encrypt only some items of genotype data. For example, the data processing device may encrypt only the genetic ID and the genetic location information. The data processing device may convert the genotype data in whole or in part, using a hash key. There are various ways to generate the hash key. Typical hash key generation algorithms include MD5 and SHA-256. The hash key is a character string of an arbitrary length. The hash key may be dynamically determined according to the configuration of biological data sets.

Furthermore, the data processing device may process the genetic ID and the genetic location information in a predetermined manner and then hash the genetic ID and the genetic location information. For example, the data processing device may concatenate the genetic ID and the genetic location information according to a predetermined rule and then hash the resulting concatenated string. For example, the data processing device hashes a genetic ID of "1" and a gene's location of "23" into an integer in a range of 0 to 4,294,967,295 so that original genotype data cannot be extracted or inferred from the integer.

The genetic variant information is expressed as a combination of bases sequence of A, G, T, and C. For example, when the type of a variant is A/T, the genetic variant information is AA, AT, or TT. The data processing device may convert each base into a binary number. The encryption result varies depending on the hash key and the encrypted genetic location information. For example, when the type of a variant at a position of 1000 on Chromosome 1 is A/T, AA may be encrypted into 00, AT into 01, and TT into 11. When the type of a variant at a position of 4000 on Chromosome 2 is A/G, AA may be encrypted into 11, AG into 01, and GG into 00.

The data processing device reduces the size of original biological data by converting the data in the form of a string into data in the form of a binary number.

FIG. 5B illustrates an example of encrypted phenotype data.

Original phenotype data may include sex, race, height, medications, and the like. The value of each data entry is a character string or a number. The data processing device hashes the phenotype data in whole or in part. For example, the data processing device group data entries of the phenotype data into classes and convert the value of each data entry into a class value. Alternatively, the data processing device may convert the value of each data entry into a binary number as in the case of the genetic variant information.

Figure 6:
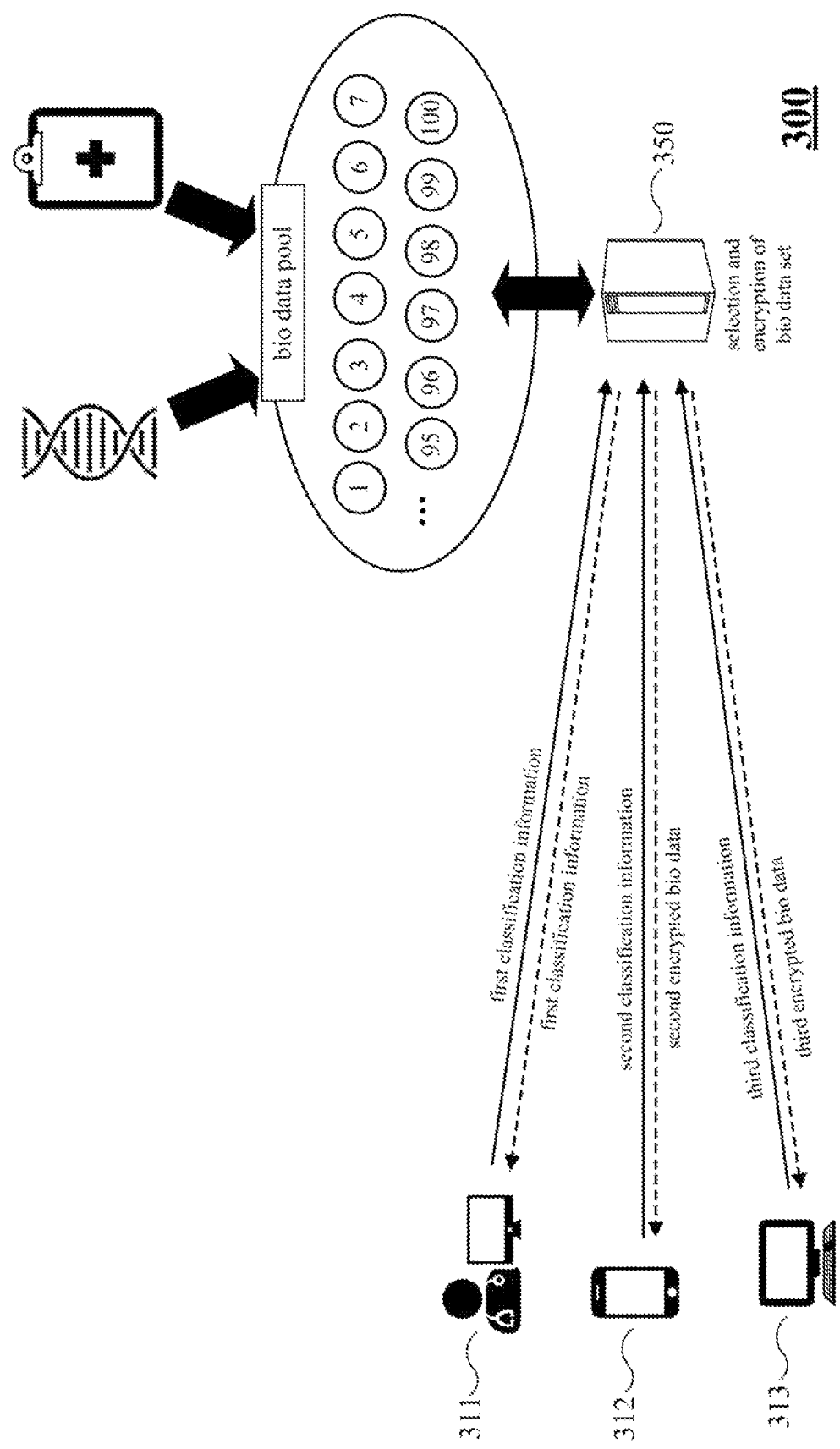
FIG. 6 is a diagram illustrating a hash key determination method according to one embodiment.

The genotype data and/or the phenotype data can be hashed in various ways. As described above, the hash key may be dynamically determined depending on the configuration of the biological data sets. FIG. 6 is a diagram illustrating a hash key determination method according to one embodiment. FIG. 6 illustrates three data analysis devices 311, 312, and 313 and a data processing device 350. In the example of FIG. 6, a biological data pool is composed of 100 biological data entries.

The data processing device 350 receives classification information from the data analysis device 311, 312, or 313. The data processing device 350 constructs a biological data set by selecting some biological data entries matched with the classification information from the biological data pool.

The classification information may be composed of at least one type of information selected from among race, age, weight, height, sex, disease status, disease type, the number of groups constituting each biological data set, and the number of data entries belonging to each group. By default, the classification information is the criteria for selecting a specific group from the biological data pool. Some examples will be described below.

(1) The data analysis device 311 transmits classification information (referred to as first classification information for convenience of description) to the data processing device 350. The biological data user requests biological data of samples that meet his or her research objective. For example, the first classification information includes the key words "Asian", "male", and "over 60 years". In this case, the data processing device 350 generates a first biological data set by selecting biological data entries matched with the classification information "Asian", "male", and "over 60 years". Next, the data processing device 350 encrypts the data entries of the first biological data set to produce encrypted biological data (for example, referred to as first encrypted biological data for convenience of description) and transfers the first encrypted biological data to the data analysis device 311. The data processing device 350 generates a first hash key for encryption, according to a combination of biological data entries constituting a biological data set. For example, the hash key may be determined using a hash function that outputs different values for different input values. The data processing device 350 generates the first hash key according to the first classification information.

(2) The data analysis device 312 transmits second classification information to the second data processing device 350. The second classification information includes the key words "normal" and "hypertensive". In this case, the data processing device 350 generates two biological data sets one of which is a biological data set composed of data entries of individuals in a healthy group and the other of which is a biological data set composed of data entries of individuals in a patient group with hypertension from the biological data pool. In this case, according to the biological data pool used, the number of data entries in the patient group varies. The data processing device 350 generates a hash key (referred to as a second hash key for convenience of description) for encryption according to a combination of biological data entries that constituting a biological data set. Alternatively, the data processing device 350 may generate the second hash key according to the second classification information. Further alternatively, the data processing device 350 may generate the second hash key according to the number of groups (for example, two groups including a healthy group and a patient group with hypertension). Further alternatively, in order to generate the second hash key, the data processing device 350 may additionally use information on the number of data entries belonging to the patient group with hypertension or information on the number of data entries belonging to the healthy group. Next, the data processing device 350 encrypts the data entries included in the selected biological data set to produce encrypted biological data (referred to second encrypted biological data for convenience of description) and transfers the second encrypted biological data to the data analysis device 312.

(3) The data analysis device 313 transmits third classification information to the data processing device 350. The third classification information includes, for example, the key words "30 males" and "25 females". In this case, the data processing device 350 generates a biological data set by selecting data entries of 30 male individuals and data entries of 25 female individuals from a biological data pool. The data processing device 350 generates a hash key (referred to as a third hash key for convenience of description) for encryption, according to a combination of data entries constituting a biological data set. Alternatively, the data processing device 350 may generate the third has key according to the third classification information. Further alternatively, the data processing device 350 may generate the third hash key according to the number of groups (for example, two groups including a male group and a female group). The data processing device 350 may generate the third hash key according to the number of data entries belonging to the male group or the number of data entries belonging to the female group.

Further alternatively, the data processing device 350 may determine a hash key by using time information such as the time at which the classification information is received or the time at which the encryption is performed, as an additional variable.

A certain data entry may be included in all of the biological data sets respectively requested by the data analysis devices 311, 312, and 313 according to the classification information. For example, it is assumed that a biological data entry labeled with number 10 is included in all of the requested biological data sets. In this case, although the same biological data (i.e., the data entry of number 10) is requested by the respective data analysis devices 311, 312, and 313, the biological data sets requested by the data analysis devices 311, 312, and 313 differ from each other because the biological data sets are constructed according to different kinds of classification information. Therefore, the hash keys used to encrypt the biological data sets respectively requested by the data analysis devices 11, 312, and 313) also differ from each other. As a result, the same biological data in the data entry of number 10 is transmitted as different values to the data analysis devices 311, 312, and 313.

Figure 7:
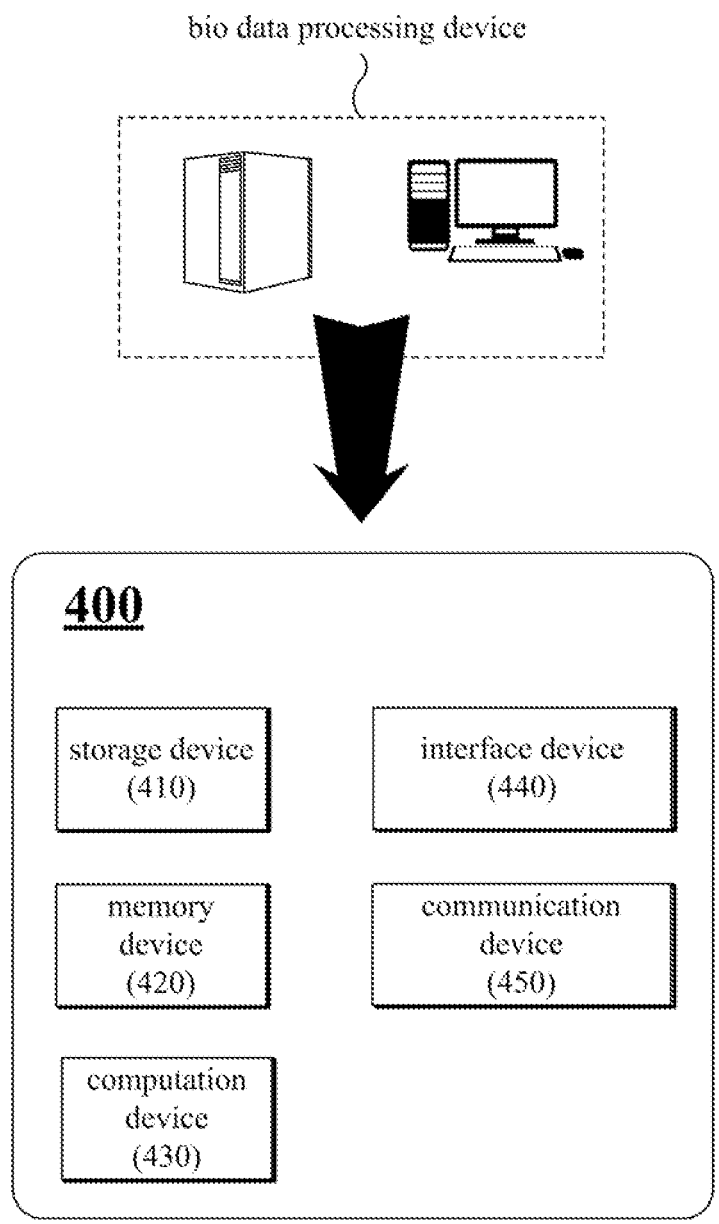
FIG. 7 is a diagram illustrating the construction of a biological data processing device according to one embodiment.

FIG. 7 is a diagram illustrating the construction of a biological data processing device 400 according to one embodiment. The biological data processing device 400 corresponds to a device used by the service provider 10 or 50 described above. The biological data processing device 400 corresponds to the biological data processing device 130 or 350 described above.

The biological data processing device 400 processes biological data using a biological data processing model or a biological data processing program. The biological data processing device 400 can be implemented in various physical forms. For example, the biological data processing device 400 may be implemented in the form of a PC, a smart device, a computer device, a network server, a dedicated data processing chipset, or the like.

The biological data processing device 400 includes a storage device 410, a memory device 420, a computation device 430, an interface device 440, and a communication device 450.

The storage device 410 stores a biological data pool. The storage device 410 stores a program for encrypting biological data included in a biological data set selected from the biological data pool. In addition, the storage device 410 stores a program for pre-processing (normalization) of data and a program for post-processing (format conversion) of data. The storage device 410 stores selected biological data sets and encrypted biological data sets. In addition, the storage device 410 stores a mapping table in which original values of biological data and hash values of the biological data are associated with each other.

The memory device 420 stores data that is used by the biological data processing device 400 during data processing and temporary data that is generated by the biological data processing device 400 during the data processing.

The interface device 440 is a device for receiving predetermined instructions and data from the outside. The interface device 440 may receive, as an input, a biological data pool from an input device or an external storage device physically connected to the interface device. The interface device 440 may receive, as an input, a data processing program.

The communication device 450 refers to a device capable of receiving and transmitting information over a wired or wireless network. The communication device 450 may receive a biological data pool from an external subject. The communication device 450 may receive a data processing program and data. The communication device 450 may receive classification information as criterion for selection of biological data sets. The communication device 450 may transmit encrypted data to an external subject. The communication device 450 may receive the results of analysis from the data analysis device. The communication device 450 may transmit decrypted biological data obtained by decrypting biological data included in the results of analysis to the data analysis device.

The communication device 450 and the interface device 440 are devices for receiving predetermined data and/or instructions from the outside. The communication device 450 and the interface device 440 may be referred to as an input device.

The computation device 430 uses a program to select a biological data set from a biological data pool in accordance with classification information. The computation device 430 uses a program to generate a hash key on the basis of classification information or a combination of biological data sets. In some cases, the computation device 430 generates the hash key by using time information in addition to the classification information or the combination of biological data sets. The computation device 430 uses a program to encrypt biological data entries included in the biological data set selected through the execution of the program.

The computation device 430 encrypts biological data, in whole or in part. For example, the computation device 430 may encrypt at least one type of information selected from among a genetic identifier, genetic location information, and genetic variant information. The computation device 430 may be a device for processing data and performing various operations. Examples of the computation device 430 may be a processor, an AP, or a program-embedded chip.

Figure 8:
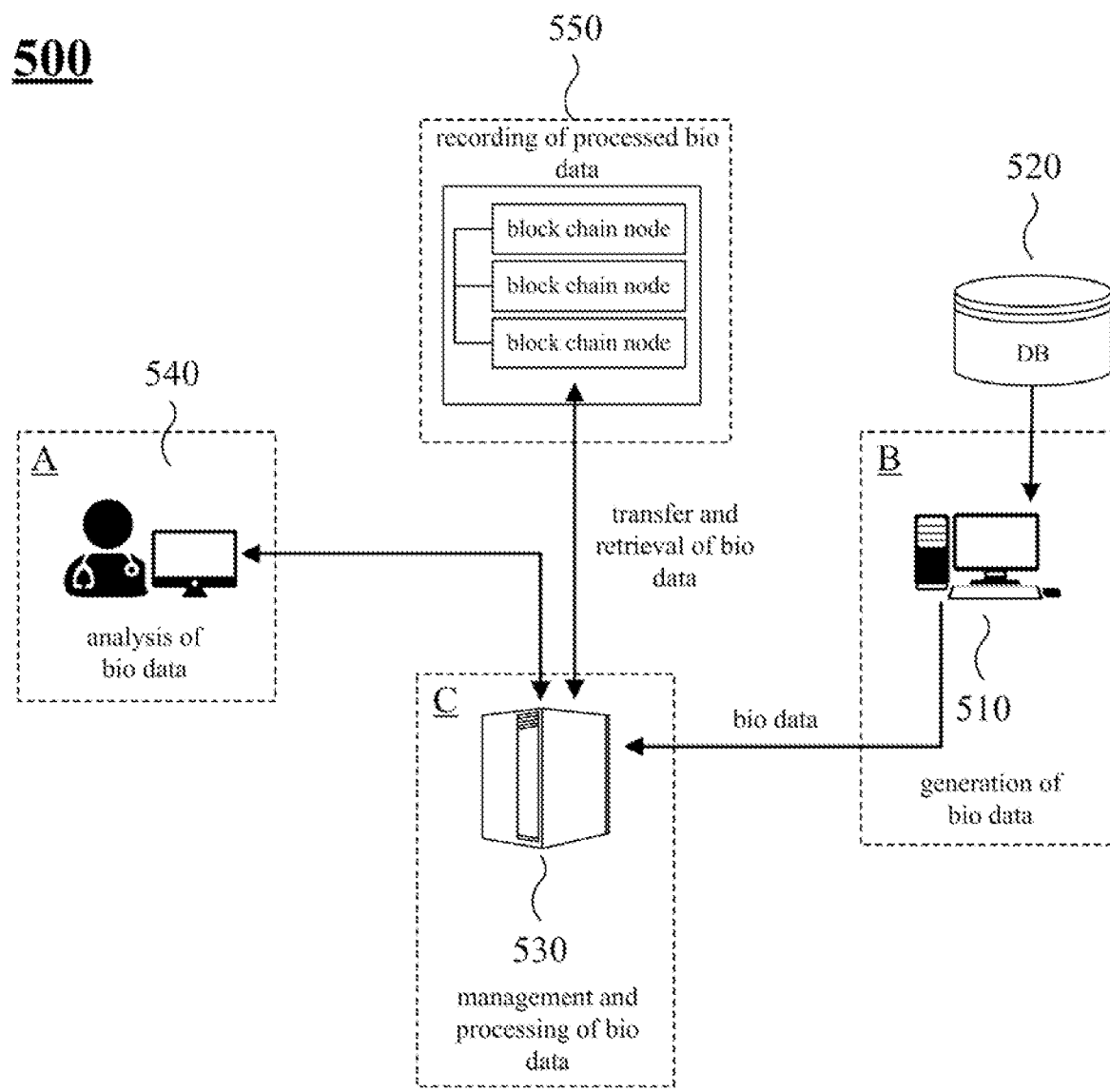
FIG. 8 is a diagram illustrating a biological data processing system according to another embodiment.

FIG. 8 is a diagram illustrating a biological data processing system 500 according to another embodiment. FIG. 8 illustrates an example in which the system stores and manages biological data, using a block chain technology. FIG. 8 illustrates a biological data user A, a biological data provider B, and a service provider C. The biological data processing system 500 includes a data generation device 510, a data processing device 530, and a data analysis device 540.

The data generation device 510 is an analyzer for analyzing a sample. For example, the data generation device 500 includes a next-generation sequencing (NGS) analyzer. The data generation device 500 generates genotype data. The data generation device 510 receives phenotype data of subjects from a medical database 520. The data generation device 510 generates biological data composed of genotype data and phenotype data. Alternatively, the data generation device 510 may generate biological data composed of only genotype data.

The data processing device 530 processes the biological data generated by the data generation device 510. The data processing device 530 encrypts the biological data, in whole or in part. The data processing device 530 hashes the biological data using a predetermined hash key. The data processing device 530 stores the processed biological data in the form of a block chain 550. That is, a biological data pool is stored in the block chain 550. The data processing device 530 extracts a specific biological data entry or a biological data set from the block chain 550. The data processing device 530 updates a specific biological data entry stored in the block chain 550.

The data analysis device 540 can analyze the biological data that is in an encrypted form. The data analysis device 540 transmits the results of analysis to the data processing device 530. The data processing device 530 decrypts the encrypted biological data included in the results of analysis, and transfers the obtained biological data to the data analysis device 530.

Although not illustrated in FIG. 8, the data generation device 510 may store biological data composed of genotype data and phenotype data of a sample in the block chain 550. The data generation device 510 transfers biological data belonging to a biological data pool to the block chain 550. The block chain 550 contains the biological data pool. The data analysis device 540 may have access to the block chain 550 to extract a biological data set from the block chain 550 as necessary and encrypt the extracted biological data set. The data analysis device 540 may store the biological data set including encrypted biological data back into the block chain 550. In this case, one biological data set may be stored in a single block or distributed in multiple consecutive blocks in the block chain 550.

The data analysis device 540 may have access to the block chain 550 to extract encrypted biological data. The data analysis device 540 may store the results of analysis back into the block chain 550. The data processing device 530 may have access to the block chain 550 to decrypt the encrypted data contained in the analysis results and transfer the decrypted data to the data analysis device 540. Alternatively, the data processing device 530 may store the encrypted data into the block chain 550.

The biological data encryption method, the biological data processing method, and the hash key determination method can be implemented as a program (or application) including an algorithm that can be executed by a computer. The program may be stored in a non-transitory computer-readable medium.

A non-transitory readable medium is a semi-permanent storage medium that can be read by a device rather than a temporary storage medium such as a register, a cache, or a memory. Specifically, various applications or programs described above may be stored in a non-transitory readable medium, such as a CD, a DVD, a hard disk, a Blu-ray disk, a USB, a memory card, or a ROM.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of providing biological data, the method comprising:
   receiving, by a data processing device, classification information from a user;
   extracting, by the data processing device, a biological data set selected from a biological data pool based on the classification information;
   encrypting, by the data processing device, biological data of the biological data set to produce encrypted biological data using a key, wherein a value of the key is determined by the classification information;
   transferring, by the data processing device, the encrypted biological data to the user;
   receiving, by the data processing device, a result of analysis which is performed using the encrypted biological data from the user;
   decrypting, by the data processing device, at least some of the encrypted biological data in the result of analysis; and
   transferring, by the data processing device, the decrypted biological data to the user,
   wherein the biological data set comprises biological data for a plurality of subjects, and
   wherein the classification information comprises at least two information types of the classification information selected from a group of information types consisting of race, age, weight, height, sex, disease status, disease type, type of subject, and a number of the plurality of subjects.

2. The method according to claim 1, wherein the biological data includes at least one type of data selected from among genotype data, phenotype data, and medical data.

3. The method according to claim 1, wherein the key is further determined according to time at which the classification information is received or the encryption is performed.

4. The method according to claim 1, wherein the data processing device encrypts at least one item of genetic variant information comprising a genetic identifier, a genetic location, and a genetic trait, among items of the biological data.

5. The method according to claim 1, wherein the data processing device stores the encrypted biological data in a block chain.

6. A method of encrypting biological data, the method comprising:
   receiving, by a data processing device, a biological data pool;
   receiving, by the data processing device, classification information from a user;
   selecting, by the data processing device, a biological data set from the biological data pool according to the classification information; and
   encrypting, by the data processing device, each biological data entry included in the biological data set using a key, wherein a value of the key is determined by the classification information,
   wherein the biological data set comprises biological data for ach of a plurality of subjects, and
   wherein the classification information comprises at least two information types of the classification information selected from a group of information types consisting of race, age, weight, height, sex, disease status, disease type, type of subject, and a number of the plurality of subjects.

7. The method according to claim 6, wherein the biological data comprises at least one type of data selected from among genotype data, phenotype data, and medical data.

8. The method according to claim 6, wherein the key is further determined according to time at which the classification information is received or the encryption is performed.

9. The method according to claim 6, wherein the data processing device encrypts at least one item of genetic variant information comprising a genetic identifier, a genetic location, and a genetic trait, among items of the biological data.

10. A biological data processing device comprises:
- a storage device configured to store a biological data pool and a program for encrypting biological data included in a biological data set; and
- a processor configured to select the biological data set from the biological data pool according to classification information, and encrypt the biological data included in the biological data set with a key by the program, wherein a value of the key is determined by the classification information,
- wherein the biological data set comprises the biological data for each of a plurality of subjects, and
- wherein the classification information comprises at least two information types of the classification information selected from a group of information types consisting of race, age, weight, height, sex, disease status, disease type, type of subject, and a number of the plurality of subjects.

11. The device according to claim 10, wherein the processor is further configured to determine the key according to time at which the classification information is received or the encryption is performed.

12. The device according to claim 10, further comprising a communication device configured to transmit the encrypted biological data.

13. The device according to claim 12,
- wherein the storage device further configured to stores a table containing hash values for the biological data and original values for the biological data;
- wherein the communication device further configured to receive a result of analysis on the encrypted biological data; and
- wherein the processor further configured to decrypt the encrypted biological data included in the result of the analysis by using the table.

14. The device according to claim 10, wherein the processor configured to encrypt at least one item of genetic variant information comprising a genetic identifier, a genetic location, and a genetic trait, among items of the biological data.

* * * * *